(12) United States Patent
Schmidt et al.

(10) Patent No.: US 10,687,719 B2
(45) Date of Patent: Jun. 23, 2020

(54) IMPLANTABLE SHUNT SYSTEM AND ASSOCIATED PRESSURE SENSORS

(71) Applicant: THE ALFRED E. MANN FOUNDATION FOR SCIENTIFIC RESEARCH, Santa Clara, CA (US)

(72) Inventors: Siegmar Schmidt, Simi Valley, CA (US); Charles L. Byers, Canyon Country, CA (US); Guangqiang Jiang, Valencia, CA (US); Brian R. Dearden, Pasadena, CA (US); John C. Gord, Venice, CA (US); Daniel Rodriguez, Camarillo, CA (US)

(73) Assignee: The Alfred E. Mann Foundation for Scientific Research, Santa Clarita, CA (US)

( * ) Notice: Subject to any disclaimer, the term of this patent is extended or adjusted under 35 U.S.C. 154(b) by 518 days.

(21) Appl. No.: 15/641,174

(22) Filed: Jul. 3, 2017

(65) Prior Publication Data
US 2017/0354337 A1 Dec. 14, 2017

Related U.S. Application Data

(62) Division of application No. 13/984,826, filed as application No. PCT/US2012/025527 on Feb. 16, 2012, now Pat. No. 9,713,429.

(Continued)

(51) Int. Cl.
*A61B 5/03* (2006.01)
*A61B 5/07* (2006.01)
(Continued)

(52) U.S. Cl.
CPC .............. *A61B 5/031* (2013.01); *A61B 5/076* (2013.01); *A61B 5/686* (2013.01); *A61M 27/006* (2013.01);
(Continued)

(58) Field of Classification Search
CPC ....... A61B 5/031; A61B 5/076; A61B 5/0031; A61B 5/686; A61B 2560/0204;
(Continued)

(56) References Cited

U.S. PATENT DOCUMENTS 3,697,917 A 10/1972 Orth et al.
3,876,408 A 4/1975 Geyer
(Continued)

FOREIGN PATENT DOCUMENTS

DE 102007008642 B3 8/2008
EP 1491137 A2 12/2004
(Continued)

OTHER PUBLICATIONS

International Search Report and Written Opinion, International Application No. PCT/US/2012/025527, dated Sep. 25, 2012.

*Primary Examiner* — Devin B Henson
(74) *Attorney, Agent, or Firm* — Lewis Roca Rothgerber Christie LLP

(57) ABSTRACT

A hermetically sealed biocompatible pressure sensor module configured for implant at a desired site at which a pressure is to be measured. Anodic bonding of the pressure module package components which have similar thermal coefficients of expansion provides low stress bonding and maintains long term reliability, dependability and accuracy. The pressure sensor module includes a pressure sensitive membrane which is in direct contact with the environment at which a pressure is to be measured. The pressure sensor module forms a part of a pressure measuring system which uses a telemetry link between the pressure sensor module and an external controller for data transmission and transfer. Operating power for the pressure sensor module is provided by the external controller and an internal rechargeable energy storage component. Accordingly, the pressure measuring system provides a dual stage power and data transfer (Continued)

capability for use with an implantable system. An exemplary use of the pressure sensor module is in a three pressure sensor system including a flow control valve in a shunt to treat hydrocephalus. The use of integrated circuit chips and an internal coil with an optional ferrite core in the pressure sensor module provides for low power consumption and reliable signal processing. An embodiment of the invention includes a pressure sensor and associated electromagnetic coils embedded in the tip portion of the shunt for measuring the pressure of fluid externally of the shunt at the tip portion.

22 Claims, 19 Drawing Sheets

Related U.S. Application Data

(60) Provisional application No. 61/443,508, filed on Feb. 16, 2011, provisional application No. 61/443,535, filed on Feb. 16, 2011.

(51) Int. Cl.
  *A61B 5/00* (2006.01)
  *H02J 50/00* (2016.01)
  *H02J 50/40* (2016.01)
  *A61M 27/00* (2006.01)
  *H02J 50/10* (2016.01)
  *A61N 1/378* (2006.01)
  *A61N 1/372* (2006.01)

(52) U.S. Cl.
  CPC .......... *A61B 5/0031* (2013.01); *A61B 5/6864* (2013.01); *A61B 5/6865* (2013.01); *A61B 5/6868* (2013.01); *A61B 2560/0219* (2013.01); *A61N 1/3787* (2013.01); *A61N 1/37229* (2013.01); *H02J 50/005* (2020.01); *H02J 50/10* (2016.02); *H02J 50/40* (2016.02)

(58) Field of Classification Search
  CPC .......... A61B 2560/0219; A61N 1/3787; A61N 1/37229; H02J 50/005; H02J 50/10; H02J 50/40
  See application file for complete search history.

(56) References Cited

U.S. PATENT DOCUMENTS

| | | | | |
|---|---|---|---|---|
| 3,958,558 | A | 5/1976 | Dunphy et al. | |
| 4,127,110 | A | 11/1978 | Bullara | |
| 4,519,401 | A | 5/1985 | Ko et al. | |
| 4,846,191 | A | 7/1989 | Brockway et al. | |
| 5,704,352 | A | 1/1998 | Tremblay et al. | |
| 5,810,735 | A | 9/1998 | Halperin et al. | |
| 5,996,419 | A | 12/1999 | Sokn | |
| 2002/0052563 | A1 | 5/2002 | Penn et al. | |
| 2005/0027330 | A1* | 2/2005 | Govari | A61B 5/0031 607/60 |
| 2005/0187488 | A1 | 8/2005 | Wolf | |
| 2006/0208899 | A1 | 9/2006 | Suzuki et al. | |
| 2008/0058652 | A1* | 3/2008 | Payne | A61B 5/0031 600/488 |
| 2008/0139959 | A1* | 6/2008 | Miethke | A61B 5/0031 600/561 |
| 2009/0157145 | A1* | 6/2009 | Cauller | A61F 2/68 607/60 |
| 2009/0204019 | A1 | 8/2009 | Ginggen et al. | |
| 2010/0022896 | A1 | 1/2010 | Yadav | |
| 2010/0030103 | A1 | 2/2010 | Lutze et al. | |
| 2011/0278948 | A1* | 11/2011 | Forsell | H02J 50/80 307/104 |

FOREIGN PATENT DOCUMENTS

| | | | |
|---|---|---|---|
| EP | 1702641 | A2 | 9/2006 |
| EP | 2055227 | A1 | 5/2009 |
| EP | 2090330 | A1 | 8/2009 |

* cited by examiner

IMPLANTABLE SHUNT SYSTEM AND ASSOCIATED PRESSURE SENSORS

CROSS-REFERENCE TO RELATED APPLICATION(S)

This U.S. application is a Divisional of U.S. application Ser. No. 13/984,826 filed on Nov. 1, 2013, entitled IMPLANTABLE SHUNT SYSTEM AND ASSOCIATED PRESSURE SENSORS, which claims the benefit and priority of PCT Application No. PCT/US2012/025527, filed on Feb. 16, 2012, entitled IMPLANTABLE SHUNT SYSTEM AND ASSOCIATED PRESSURE SENSORS, which claims the benefit of Provisional Application No. 61/443,508, filed on Feb. 16, 2011, entitled PRESSURE SENSOR SYSTEM FOR IMPLANTED APPLICATIONS; and Provisional Application No. 61/443,535, filed on Feb. 16, 2011, entitled IMPLANTABLE SHUNT SYSTEM WITH MULTIPLE PRESSURE SENSORS, which are incorporated in their entirety herein by reference.

BACKGROUND OF THE INVENTION

Pressure sensors for implantable applications have been developed in the past. A focus of the pressure sensors in the art has been to monitor, for example, intracranial pressures, intrapleural and blood pressure. Recently, particular attention has been drawn to monitor and treat a condition known as hydrocephalus. Hydrocephalus, also known as "water in the brain," is a medical condition in which there is an abnormal accumulation of cerebrospinal fluid (CSF) in the ventricles, or cavities, of the brain. This may cause increased intracranial pressure inside the skull and progressive enlargement of the head, convulsion, tunnel vision, and mental disability. Hydrocephalus can also cause death.

Pressure sensors exist today that can be implanted inside the cranium for a short period of time up to a maximum of a few weeks, with connecting wires or conduits passing through a wound in the scalp. These devices for example, are used in treating acute conditions such as traumatic brain injury (TBI) or monitoring and diagnosing chronic conditions such as hydrocephalus. However, pressure sensors must have certain continuous, long term intracranial pressure information. Accordingly, the shortcomings of current devices creates a severe limitation in monitoring the effectiveness of ventriculoperitoneal shunts, which are commonly used in treating hydrocephalus and in treating acute brain injury. In such instances an additional concern is the replacement of short term sensors that have failed with the attendant risk of infection accompanying sensor use.

The following attributes are required for a pressure sensor in order for it to be suitable for long term implantation and monitoring applications in the brain. The pressure sensors must be diminutive in size for ease of implant as well as to minimize disturbance to the tissue environment surrounding the pressure sensor and they must use wireless communication so that no wires, conduits, or other components require a passageway through the skin. They must be formed of break-resistant, non-toxic and everlasting bio-compatible materials to minimize the patient's immune reaction to the introduction of a foreign body and to prevent tissue injury from corrosion byproducts. The implanted pressure sensor must provide pressure values that remain reliable so that treatment decisions may be made with confidence for the lifetime of the sensor to preclude sensor explant for adjustment purposes. Accordingly, the sensor must be constructed in a manner so that its measurement accuracy remains within a prescribed tolerance range independent of physical movements, temperature changes or other environmental influences it may experience. Additionally, since physiologic parameters such as internal pressures are measured with reference to local atmospheric pressure, a system utilizing an implanted pressure sensor must include provision to account for the atmospheric pressure around the patient. In such case, the use of an external controller, for example, that includes a reliable and accurate pressure sensing device is required.

There have been attempts in the past to address the issue of internal pressure measurement. For example U.S. Pat. No. 4,846,191 to Brockway et al. describes measurement of physiologic pressure by placement of a pressure transmitting catheter within a blood vessel or other structure within which pressure is to be measured. Aspects of the device include using a flexible catheter for transmitting pressure measurements from an implanted site to a pressure sensor located a distance away from the site. Typically, the pressure sensor is embedded in the scalp or just under the skin. The catheter is elongated, filled with a low viscosity fluid and is plugged with a gel. Since the catheter is compliant, the transmission of accurate and reliable pressure values is undependable. The application of fluid filled elongated catheters used in measuring pressure signals from a lateral ventricle has also been described in U.S. Pat. No. 4,519,401 to Ko and Leung. The system described in Ko also suffers from the same disadvantages as those devices in the art using fluid filled catheters in that the accuracy and reliability of pressure measurements remain undependable. Another example is U.S. Pat. No. 3,697,917 to Orth et al. that discloses a planar silicon diaphragm, anodically bonded to a cylindrical glass support and mounted in a metal tube by means of an O-ring. Deflections of the diaphragm are measured by piezoresistive strain gauges that have metal wire conductors that extend beyond the sensor housing and into the environment surrounding the housing. The device of Orth, is severely limited in its application since it is not implantable because the housing is not sealed and cannot be made hermetic due to the use and orientation of the O-ring. Yet another example is found in U.S. Pat. No. 3,958,558 to Dunphy et al. which describes a pressure transducer that includes a coaxially variable capacitor or coaxially variable inductor in alternate arrangements, wherein a bellows is mechanically coupled to the variable component to vary the value of the component in response to pressure changes of the fluid in which the bellows is immersed. Varying of the component value by the bellows, causes a change in resonant frequency of an L-C circuit which is sensed by an external source of variable frequency oscillatory energy which in turn is indicative of the level of fluid pressure being sensed. The long term reliability and accuracy of the pressure measurements of the disclosed transducer remains a question, at least, because of the involved mechanical arrangement of the bellows and the coaxially variable components will experience hysteresis and materials fatigue causing calibration drift.

SUMMARY OF THE INVENTION

The present invention is directed to a hermetically sealed bio-compatible pressure sensor ideally suited for implantable applications. Although finding utility in a myriad of monitoring and treatment strategies, the pressure sensor system herein described, finds particular use for brain implant applications, as for example, in the monitoring of pressures resulting from hydrocephalus and other intracranial pressure measuring applications. An important attribute of the present invention is the absence of any fluid filled catheters to communicate pressure values from a desired site to processing electronics. Accordingly, the implantable pressure sensor system of the present invention comprises a base plate having first and second opposite facing sides, wherein the base plate has a pressure inlet port extending through the base plate between said opposite facing sides. A pressure sensor module is mounted on the first side of the base plate and includes a pressure sensor positioned at the inlet port so as to directly measure a pressure existing at the inlet port at the second side of the base plate and to provide a pressure signal corresponding to such measured pressure.

An electronic circuit is mounted on the first side of the base plate and electrically coupled to the pressure sensor and configured to process the pressure signal appropriate for transmission to an external controller. An internal coil is mounted on the first side of the base plate and electrically coupled to the electronic circuit, said internal coil being configured to receive a power signal for providing electrical power to at least the electronic circuit and for transmitting a data signal corresponding to the pressure signal. The pressure sensor module is hermetically sealed by means of a lid secured on the first side of the base plate in a manner to provide a hermetically sealed housing for the pressure sensor, electronic circuit and the internal coil. Thus the invention contemplates a dual stage power transfer system that includes a first stage power/data transfer from the external coil to the subcutaneous outside coil wherein electromagnetic power is transferred through and across the skin covering the cranium and a second stage power/data transfer wherein electromagnetic energy is transferred from the outside coil to the internal coil.

The pressure sensor system further includes an outside coil having first and second coils, the first coil configured for placement in proximity to the internal coil for electromagnetic coupling therewith, and the second coil being positioned remotely from the first coil and configured for subcutaneous placement in proximity with a patients cranium and adapted to receive data and power signals from an external coil placed in proximity with the second coil. The pressure sensor system still further includes an external controller unit coupled to an external coil, the external coil electromagnetically coupled to the outside coil, and the controller unit being configured, at least, for receiving data signals emanating from the pressure sensor module and providing power signals to power the electronic circuit. Since the patient's physiological pressures are made with reference to atmospheric pressure, the external controller includes an atmospheric pressure sensor so as to display either: (a) the pressure measured by the pressure sensor module or (b) the difference between atmospheric pressure and the pressure measured by the pressure sensor module.

An exemplary embodiment of the invention includes the use of three pressure sensor modules disposed within a shunt that includes a fluid flow control valve. This configuration finds critical use in the treatment of hydrocephalus where it is imperative to extract excessive fluids from a patient's cranium to relieve overpressure that causes pain, improper brain functions and other tragic effects of the condition such as, permanent brain damage. The use of three pressure sensors, strategically positioned in the shunt, provides critical and reliable information regarding the overall condition of the shunt and whether the shunt is plugged, the location of the plugged portion of the shunt if that is the case and whether the valve is malfunctioning.

An embodiment of the invention includes a pressure sensor and associated magnetic coils embedded within the tip portion of the shunt for measuring fluid pressure externally of the shunt at the tip portion.

With regard to device structure, the implantable pressure sensor is configured to satisfy the United States Food and Drug Administration (FDA) rules and regulations relating to implantable devices as codified in the Code of Federal Regulations, Title 21. Moreover for the applications contemplated by the invention, the implantable pressure sensor is embedded surgically at the site desired for pressure monitoring.

DETAILED DESCRIPTION OF THE INVENTION

Figure 1:
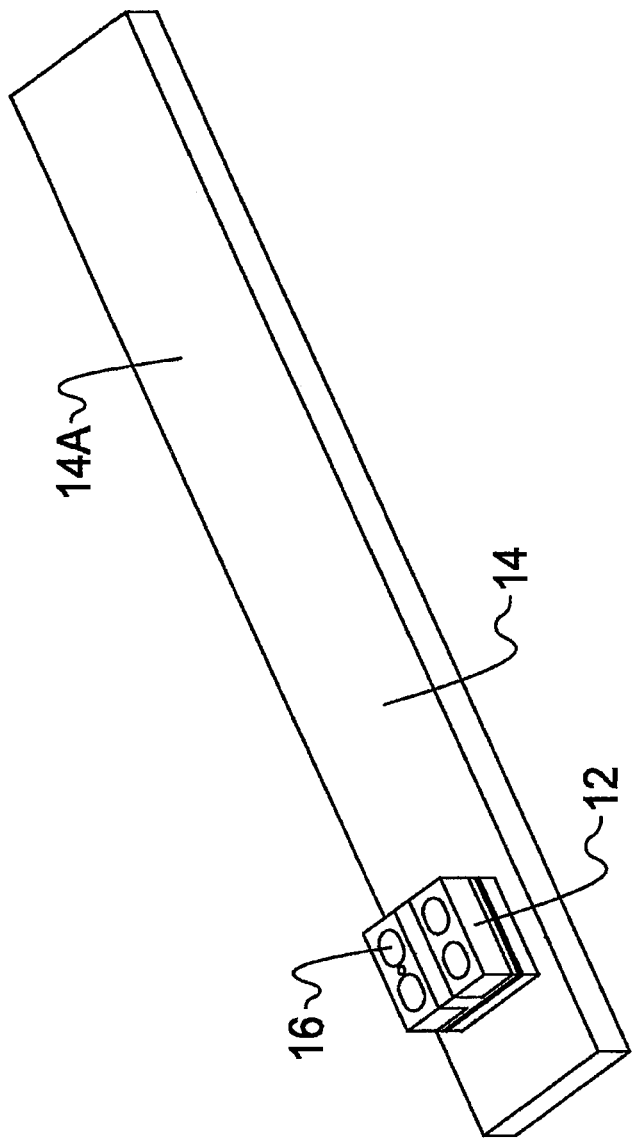
FIG. 1 is a perspective view of a pressure sensor mounted on a base plate of the pressure sensor device of the present invention.

With reference to FIG. 1, there is shown in perspective view, a pressure sensor device 12 (hereinafter identified as a "pressure sensor") mounted on an elongated base plate 14. To be discussed in more detail below, base plate 14 preferably is formed of an electrically non-conductive material such as glass. The pressure sensor 12, which is contained within a pressure sensor module 10 (see FIG. 4), may be selected from a number of commercially available silicon based pressure sensors using for example, capacitive or strain gauge pressure detecting technologies. The pressure sensor of the present invention is fabricated using micro-electro-mechanical-system or MEMS technology. Accordingly, the pressure sensors are relatively small having typical dimensions of about 2 by 2 by 1 millimeters or less. The pressure sensor of the present invention includes a pressure sensitive silicon membrane which is exposed to the environment of which the pressure is to be measured. The membrane is one element of a MEMS device with an electrode(s) disposed parallel to the membrane on the opposite side of the membrane that is exposed to the environment pressure to be measured. An attribute of the membrane is its deflection capability due to exposure to pressure and pressure changes. As long as the membrane deflects within its normal elastic range, there will be a nearly perfect linear response to applied pressure with either negligible or no measurement error due to fatigue or hysteresis. Furthermore, there are no wires extending out from the pressure sensor module 10 so as to maintain the pressure sensor module 10 hermetically sealed.

Further, in the case of a capacitor based pressure sensor, the capacitor has two electrodes 16, one of the electrodes being attached to the membrane or the electrode being the membrane itself. Any deflection of the membrane due to pressure and pressure changes causes the capacitance value of the MEMS device to change accordingly. Hence the capacitance value of the sensor changes as a function of applied pressure on the membrane which can be measured by electronic signal processing electronics. An integrated circuit (chip) coupled to the MEMS device, processes such change in capacitance value to vary the loading of an inductive coil which is further monitored by an external coil and external controller, as a measure of pressure value.

In the case of a strain gauge based pressure sensor, the strain gauges are mounted on the membrane or the membrane itself forms the strain gauge. Any deflection of the membrane under the influence of applied pressure, changes the level of strain on the gauge which can be measured accurately with conventional electronic signal measuring circuitry.

For proper operation of the pressure sensor 12, one face of the membrane (not shown) forms a wall of a sealed cavity within the pressure sensor while the other face (pressure sensing face) of the membrane is oriented so as to be exposed to the environment of which the pressure is to be measured. The pressure sensing face of the membrane may be coated with a silicone gel to protect the membrane from direct contact with body fluids and body tissue. The silicone gel coating reduces drift effects of the pressure sensor by preventing any corrosive body fluids from contacting the membrane as well as preventing cellular and tissue in-growth.

Figure 2:
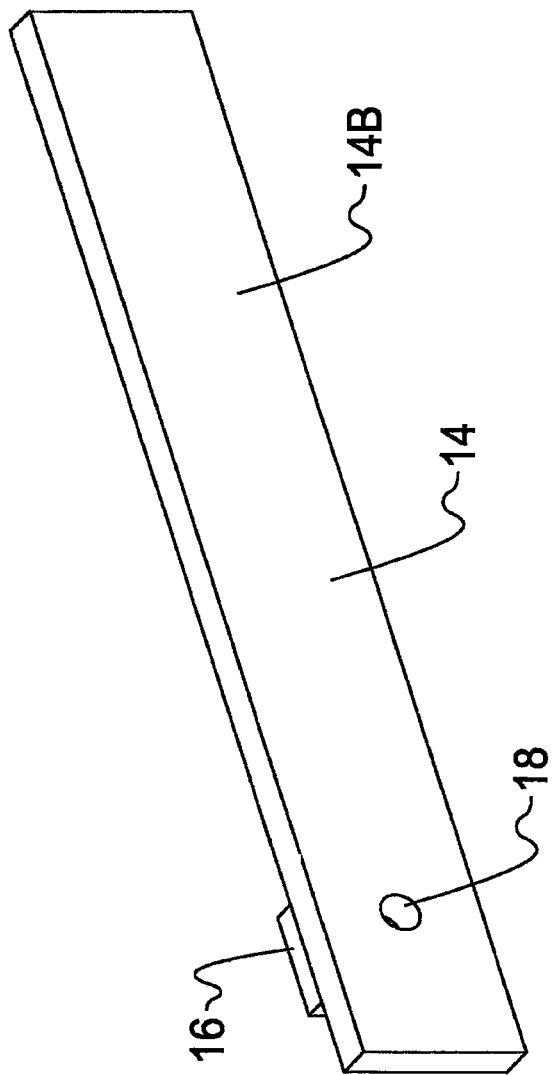
FIG. 2 is a partial perspective view of the pressure sensor device of FIG. 1 showing an aperture in the base plate for providing pressure sensing in the in vivo environment.
Figure 9:
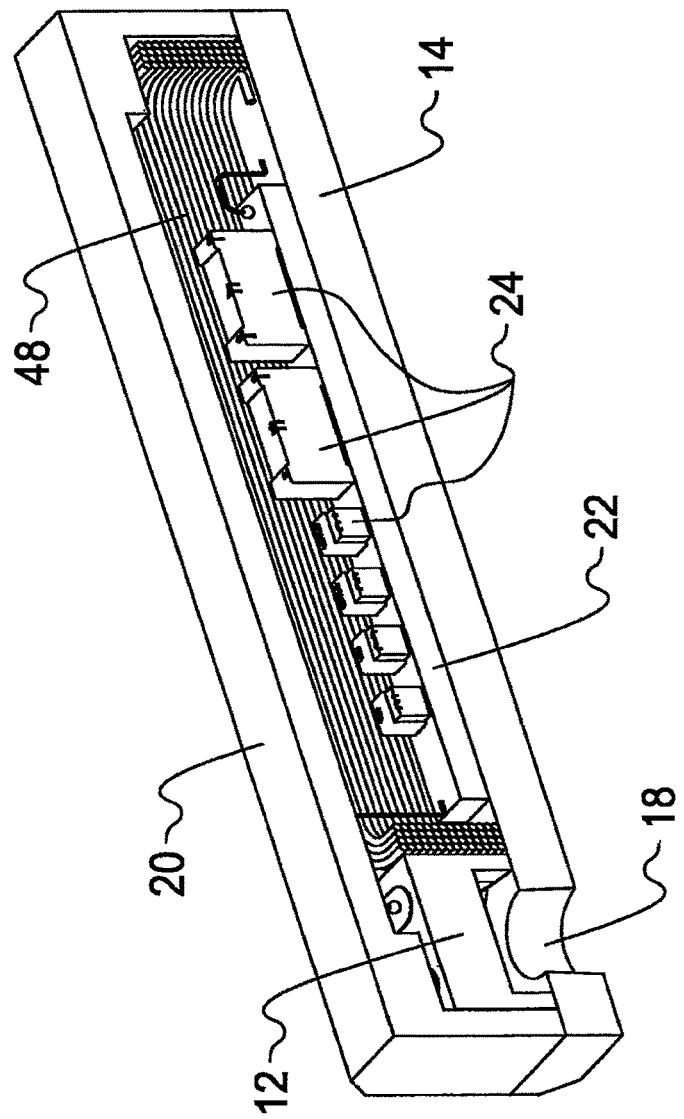
FIG. 9 is a cross sectional perspective view taken along lines A-A of FIG. 4.

Of major concern is the maintenance of long term stability of the pressure sensor 12. Accordingly, the pressure sensor 12 is mounted on the inward facing surface 14A of base plate 14 in a manner to eliminate long term changes due to residual mechanical stress from the mounting process. Furthermore, the pressure sensor 12 must be mounted in a manner to avoid any potential corrosive effects from the in vivo environment within which it operates as well as to separate any electronics components and circuitry from the in vivo environment. The preferable method of mounting the pressure sensor 12 to the base plate 14 is by anodic bonding of the silicon part of the pressure sensor 12 to the base plate 14 which may also described as a glass substrate. The benefits of anodic bonding include providing a low stress bond between the silicon portion of the pressure sensor 12 and the base plate 14 and that no dissimilar bonding material is needed between the glass and the silicon. As for the base plate 14, although selected glass compositions are acceptable, Pyrex, a Borofloat glass, SD2-Glass or one rich in sodium is preferable. The process of anodic bonding requires temperatures of about 300 to 400 degrees centigrade and voltages of about 500 to 2000 volts. The low stress hermetic bond between the pressure sensor 12 and the base plate 14, gives rise to reduced drift effects on the pressure sensor 12. Moreover, and as shown in FIG. 9 and discussed later, a silicon lid 20 is bonded to the inward facing surface 14A of base plate 14 so as to form a hermetic seal between the silicon lid 20 and base plate 14 thereby isolating the pressure sensor 12 and any associated active and passive electronics from any and all contact with corrosive fluids in the in vivo environment. As is shown in FIG. 2, the pressure sensor 12 is positioned in registration with a pressure inlet port or aperture 18 that extends between the inward facing surface 14A and outward facing surface 14B of base plate 14. The aperture 18 provides a fluid communication path between the in vivo environment and the pressure sensing face of the membrane. In this manner, the membrane is exposed to the pressure existing in the proximity of the pressure sensor 12 and corresponding pressure measurements can be accurately made.

Figure 3:
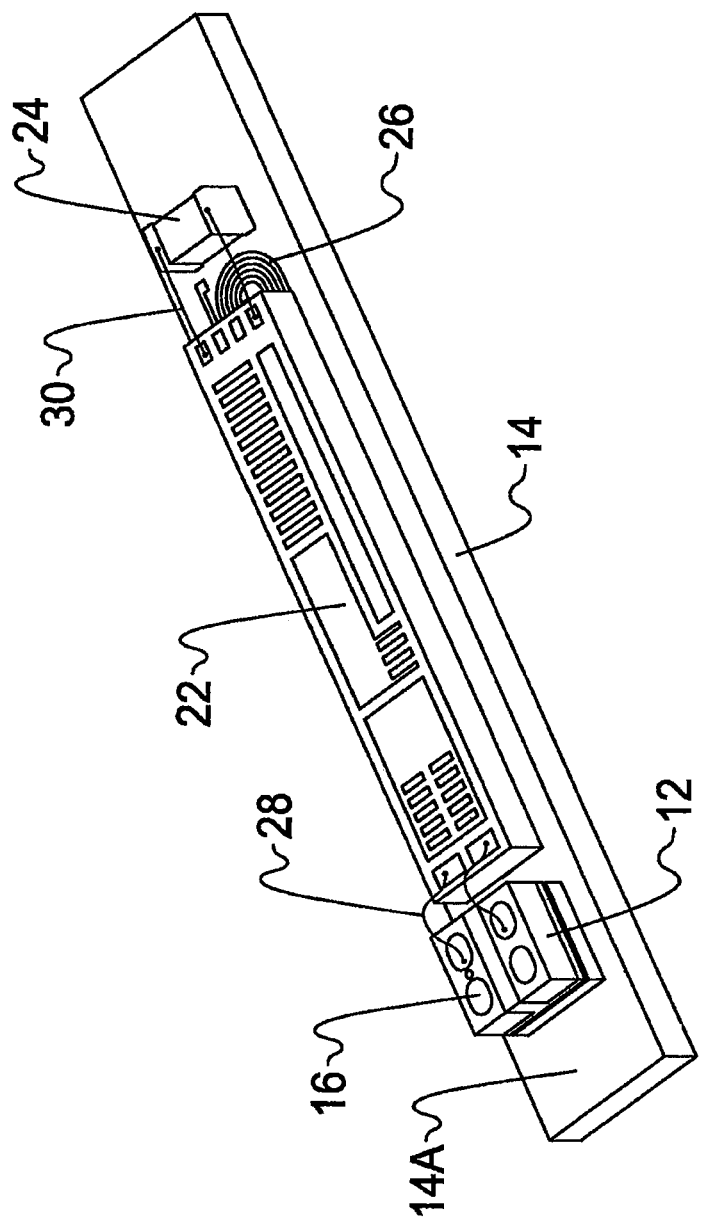
FIG. 3 is a perspective view of the base plate showing various components mounted on the base plate.

With reference to FIG. 3, there is shown an assembly of components mounted on the inward facing surface 14A of base plate 14. Mounting the components on the base plate 14 in the manner shown provides the advantage of utilizing wafer level manufacturing processes for assembling the components on a single glass plate. Within the contemplation of the invention is the use of a silicon wafer having hollow cavities that match the dimensions of the components on the base plate 14. The silicon wafer (not shown) is bonded to the base plate 14 preferably by anodic bonding. Selected components of the pressure sensor, such as for example, integrated circuits and circuit components, may then be securely mounted within the silicon wafer. An advantage of wafer level assembly is that the resultant manufacturing process is very economical.

With reference again to FIG. 3, there is shown the inward facing surface 14A upon which are mounted the pressure sensor 12, an integrated circuit 22, circuit component 24 and internal coil 26. The electrodes 16 which provide a signal path for measured pressure signals from the membrane are coupled to integrated circuit 22 by means of wire bonds 28. Integrated circuit 22 includes electronic circuits that provide signal conditioning for the output signals of pressure sensor 12 corresponding to the pressure measurements, RF oscillator circuits to further condition the output signals in preparation for transmission to an external receiving device and rectifying and energy storage circuitry to provide power sources for the electronic circuits contained within the integrated circuit 22. Further mounted on inward facing surface 14A are circuit component 24 and internal coil 26.

Circuit component 24 may be in the form of filter capacitors and internal coil 26 may be in the form of a multi-winding dual purpose coil to receive externally supplied AC signals for rectification in the integrated circuit 22 to provide operating power for the electronic circuitry as well providing a transmission antenna to transmit signals representative of detected and measured pressure signals. The integrated circuit 22 is coupled to circuit components 24 by means of wire bonds 30. Circuit components 24 may also be stacked, including stacked upon an integrated circuit chip 22.

Figure 4:
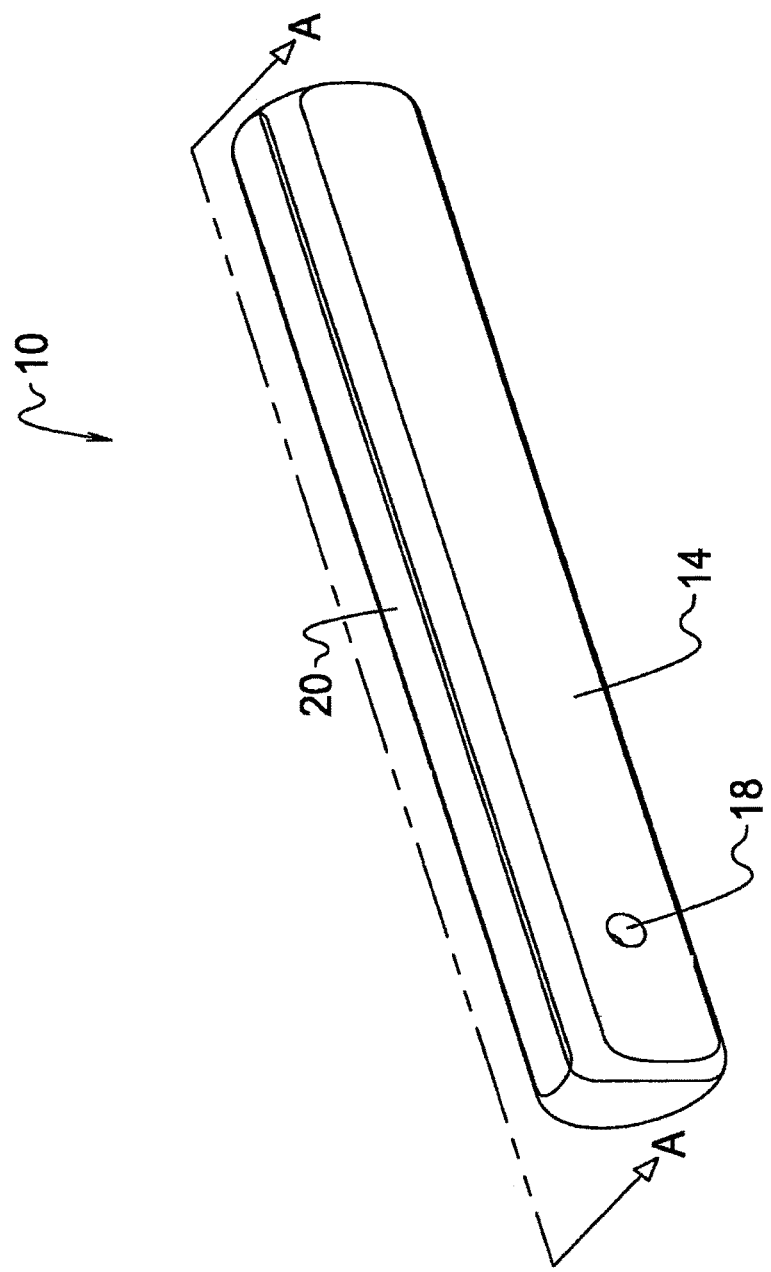
FIG. 4 is a perspective view of pressure sensor device including a lid attached to the base plate of FIG. 1.

With reference to FIG. 4, there is shown in perspective view a pressure sensor module 10 that includes a lid 20 secured to the inward facing surface of base plate 14. As previously described, lid 20 preferably is formed of silicon and secured to base plate 14 by means of a low stress anodic bonding process. The low stress bonding process insures against undesirable drift effects impacting the response of the pressure sensor 12. As shown in FIG. 4, the lid 20 completely encapsulates the components shown in FIG. 3 and provides a hermetically sealed container for the components to isolate them and make the pressure sensor module 10 impervious to fluids existing within the in vivo environment. Further shown in FIG. 4 is aperture 18 which provides a fluid communication path between the pressure sensing surface of a pressure sensor membrane (not shown) and the adjacent in vivo environment. In this manner the ambient pressure existing directly at the desired site can be measured by the pressure sensor without the environment introducing body fluids within the pressure sensor module 10. Moreover, since the pressure sensor is located directly at the desired site for pressure measurement, the need for fluid filled catheters to communicate pressure values at the site to processing electronics is obviated.

Figure 5:
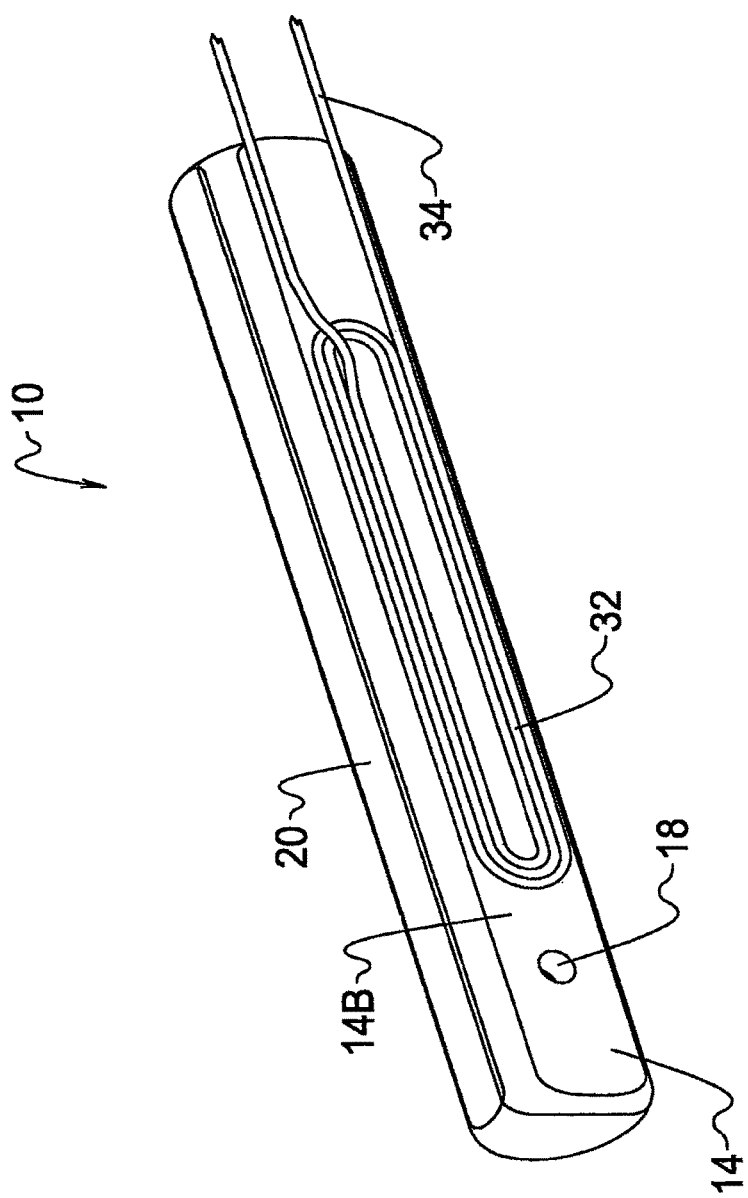
FIG. 5 is a perspective view of an outside coil attached to the base plate of the pressure sensor device of FIG. 4.

As shown in FIG. 5, positioned next to the pressure sensor outward facing surface 14B is an outside coil 32 positioned essentially in alignment with internal coil 26 so as to provide efficient electromagnetic coupling between the internal and outside coils. The outside coil 32 is multifunctional in that an AC signal applied to the coil may be coupled to the internal coil 26 for conversion in order to provide electrical power for operation of the integrated circuit 22. Additionally, storage capacitors coupled to or contained within the integrated circuit 22 may be sufficiently charged during application of the AC signal so as to provide operating power to the integrated circuit 22 during periods of time after application of the AC signal terminates. Furthermore, outside coil 32 is adapted to receive data signals, preferably digital RF signals from the internal coil 26 that are representative of pressure measurements made by pressure sensor 12 and which are converted to RF signals by integrated circuit 22. Coupling and transmission of RF signals between the internal coil 26 and the outside coil 32 may be undertaken in a manner known to those skilled in the art. Moreover conversion of pressure measurements by the pressure sensor 12 ultimately into RF signals for application to the internal coil 26 is also within the capability of those skilled in the art.

Figure 6:
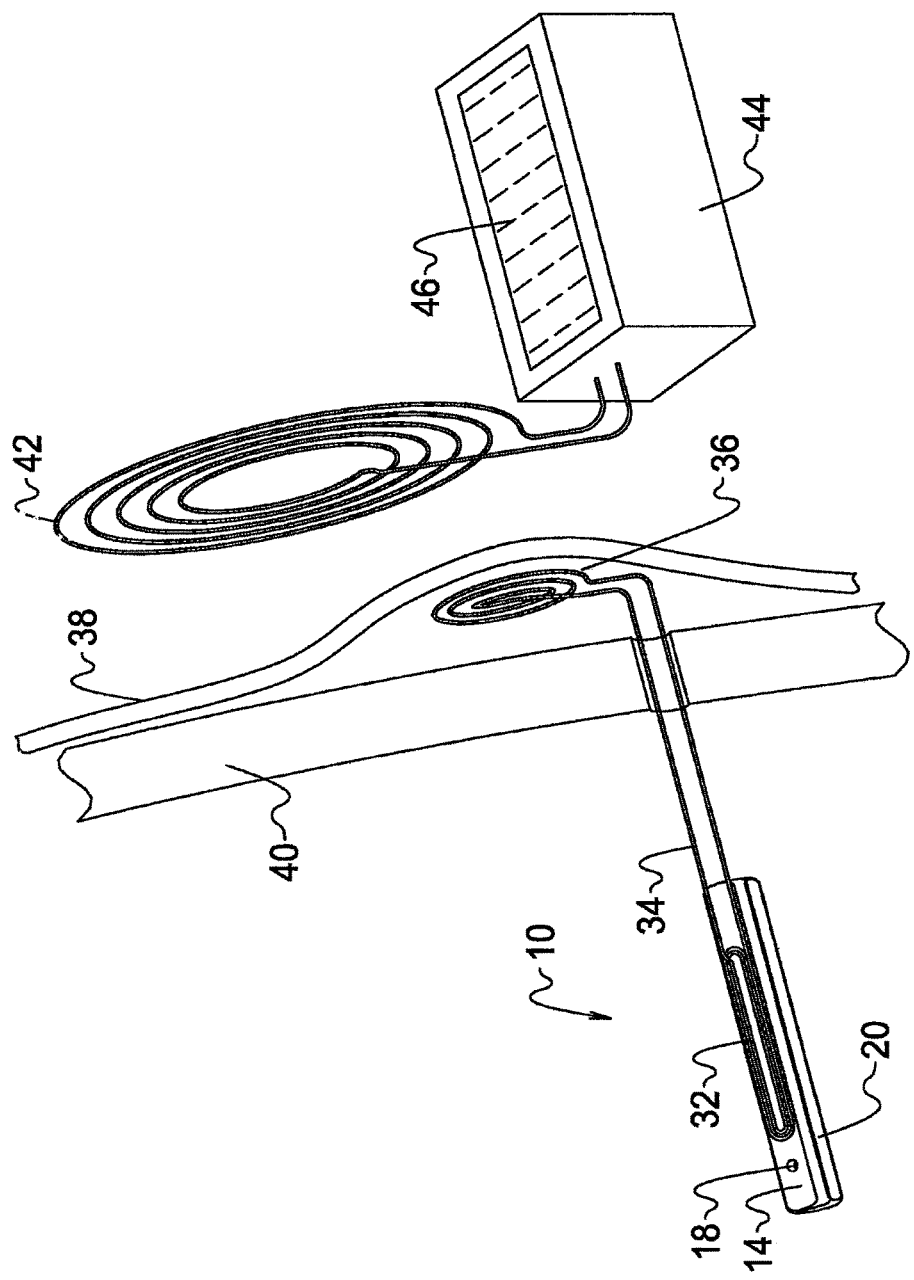
FIG. 6 is a view of an intracranial pressure monitoring system including a pressure sensor device, external coil and an external controller.

With reference to FIG. 6, coupled to outside coil 32 are electrically conductive leads 34 capable of signal transfer from the outside coil 32 to a subcutaneous coil 36. For cranial applications, the subcutaneous coil 36 preferably is positioned between the skin 38 and the bone that forms cranium 40. The length of leads 34 provide for the pressure sensor module 10 to be positioned away from the cranium in applications where such distance is necessary. Although not shown in FIG. 6, leads 34 may be somewhat coiled to provide strain relief in those instances when the pressure sensor module 10 moves relative to the position of the subcutaneous coil 36 as a result, for example, of body movement. For purposes of pressure signal transfer and power transfer, an external coil 42 may be positioned, either temporarily or semi-permanently on the external part of skin 38 and in functional registration with subcutaneous coil 36. Electromagnetic coupling between external coil 42 and subcutaneous coil 36 provides for the transfer of power and data signals between the coils. The external coil 42 is electrically coupled to and receives power/data signals from an external controller 44. Accordingly, the arrangement of FIG. 6 may be characterized as a dual stage power/data transfer wherein a first stage transfer occurs between external coil 42 and subcutaneous coil 36 and a second power/data transfer occurs between outside coil 32 and internal coil 26.

External controller 44 is configured to provide an AC power signal as well as to exchange information with the pressure sensor module 10. The external controller 44 senses the measured pressure by means of the integrated circuit and coil coupling arrangement described above and displays such pressure on a display screen 46. In addition to sensing measured pressure, external controller 44 senses temperature and other parameter information provided by pressure sensor module 10 and provides a display of such parameter information on display screen 46. The external controller 44 includes a dedicated pressure sensor (not shown) to measure atmospheric pressure. Accordingly, in the case for example of measuring intracranial pressure, the external controller 44 can measure and display the absolute intracranial pressure or the difference between the intracranial pressure and the external atmospheric pressure. The intensity of the AC charging signals may also be varied by external controller 44. Pressure sensor device parameters such as integrated circuit amplifier gain values as well as signal threshold values, for example, may be adjusted if necessary by external controller 44.

The external controller 44 is sized such that it may be conveniently hand held and preferably includes external coil 42 so that a user may easily position the external controller 44 adjacent the scalp under which subcutaneous coils 36 are located. When the external controller 44 detects that it is within a satisfactory communication range with subcutaneous coils 36, the external controller 44 transmits a power signal for a preset time period and waits for response signals from the pressure sensor module(s) 10. In the instance when multiple pressure sensor modules are utilized, the pressure sensor module(s) 10 may be configured to transmit response and parameter signals and information sequentially so that a signal train from one pressure sensor module 10 does not interfere with a signal train from another pressure sensor module 10. Besides having a display screen 46 to provide information visually, the external controller 44 may provide an audible indication when expected information or even unexpected information such as error signals have been received. Other attributes of the external controller 44 include the capability of processing the received information into selectable user friendly formats and securely storing and wirelessly transmitting processed parameter information with corresponding time and date stamps. The external controller 44 may be powered by an internal rechargeable power source or a replaceable power source.

Figure 7:
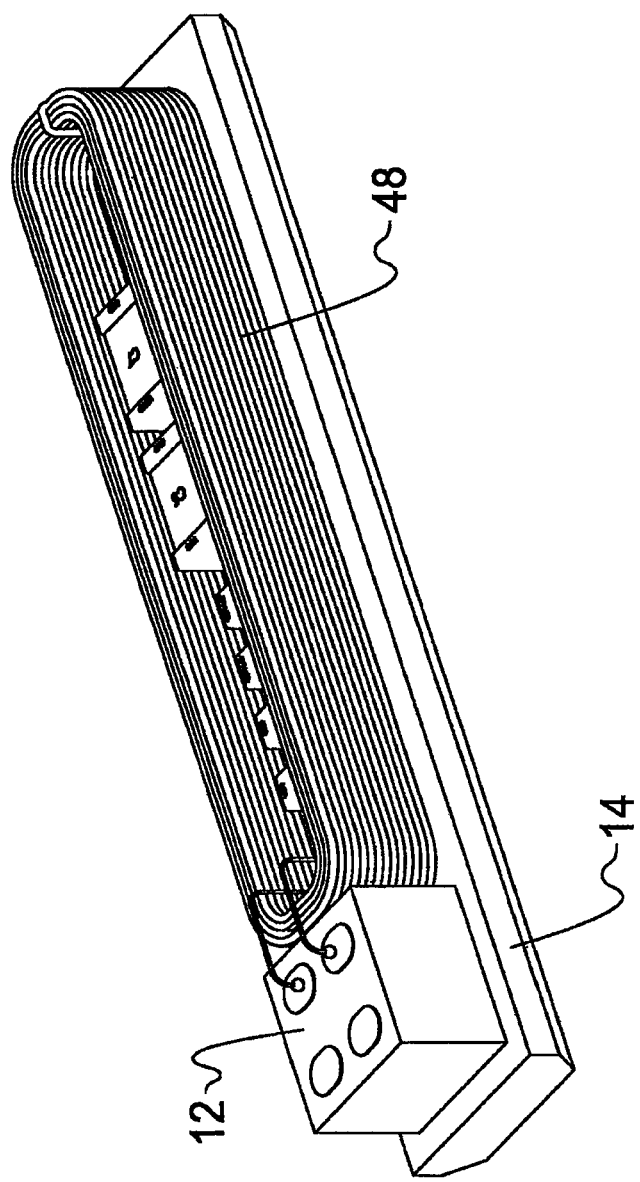
FIG. 7 is a perspective view of a pressure sensor, circuit components and internal coil mounted on the base plate of FIG. 1.

Alternate embodiments of the present invention are also contemplated as disclosed below. For example, the internal coil 26 as shown in FIG. 3, wrapped so as to be flush and in complete contact with inward facing surface 14A may be wrapped in a substantially rectangularly looped manner and extending away from surface 14A as shown in FIG. 7. Additionally, the internal coil 48 (see FIG. 7) may be wrapped around a ferrite core (not shown) so that the ferrite core serves to concentrate the electromagnetic fields surrounding the internal coil 48 so as to enhance signal generation within the coil resulting from exposure to such electromagnetic fields. The coupling efficiency between the internal coil 48 and the electromagnetic fields surrounding the coil is markedly improved particularly if the internal coil 48 is wrapped around the ferrite core and the coil 48 is aligned with external coil 42. The use of integrated circuit chips and an internal coil with a ferrite core in the pressure sensor module 10 provides for low power consumption and reliable signal processing. Since the internal coil 48 is mounted around and preferably in contact with the integrated circuit 22, the overall length of the pressure sensor module 10 may be reduced. An illustration of the outward facing surface of base plate 14 showing aperture 18, internal coil 48 and pressure sensor 12, is shown in the perspective side view of FIG. 8.

Figure 8:
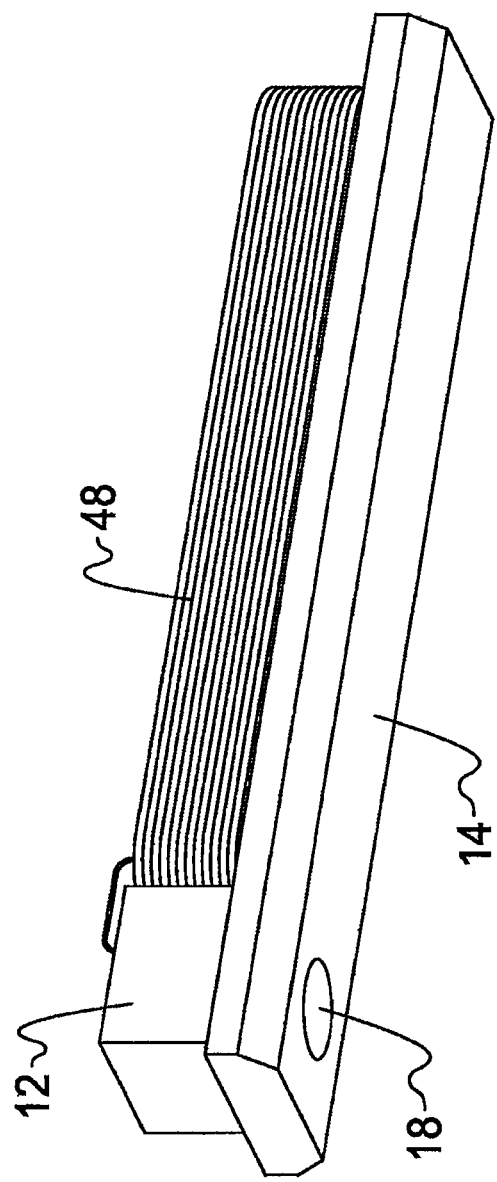
FIG. 8 is a perspective view of FIG. 7 showing the aperture in the base plate.

Referring to FIG. 9 there is shown a front cross-sectional view of the pressure sensor module 10 illustrating the assembly depicted in FIGS. 7 and 8. As previously noted, aperture 18 provides a fluid communication path from the in vivo environment to pressure sensor 12. As noted above, the internal coil 48 is shown as being mounted around integrated circuit 22 as a method of compacting packaging of the internal components to thereby reduce the overall length of the pressure sensor module 10.

Figure 10:
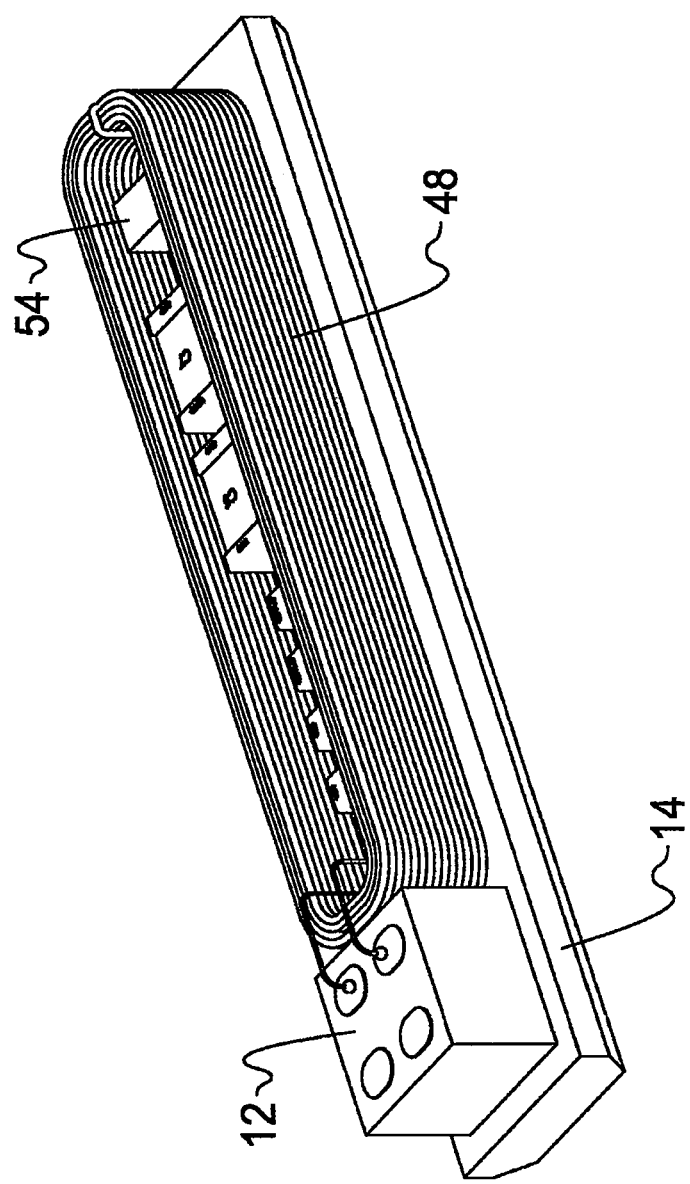
FIG. 10 is a perspective view of the glass plate showing a battery or high capacity capacitor mounted on the base plate.

Referring to FIG. 10 there is shown a perspective view of an arrangement of internal components of the pressure sensor module 10 with the inclusion however of a battery 54, preferably a rechargeable battery, or a high energy storage device such as a high energy storage capacitor. Rechargeable batteries are known in the art and provide a dependable long term energy source to support reliable operation of the pressure sensor module 10 for extended periods of time without the need of frequent charging by means of an AC electromagnetic field.

Figure 11:
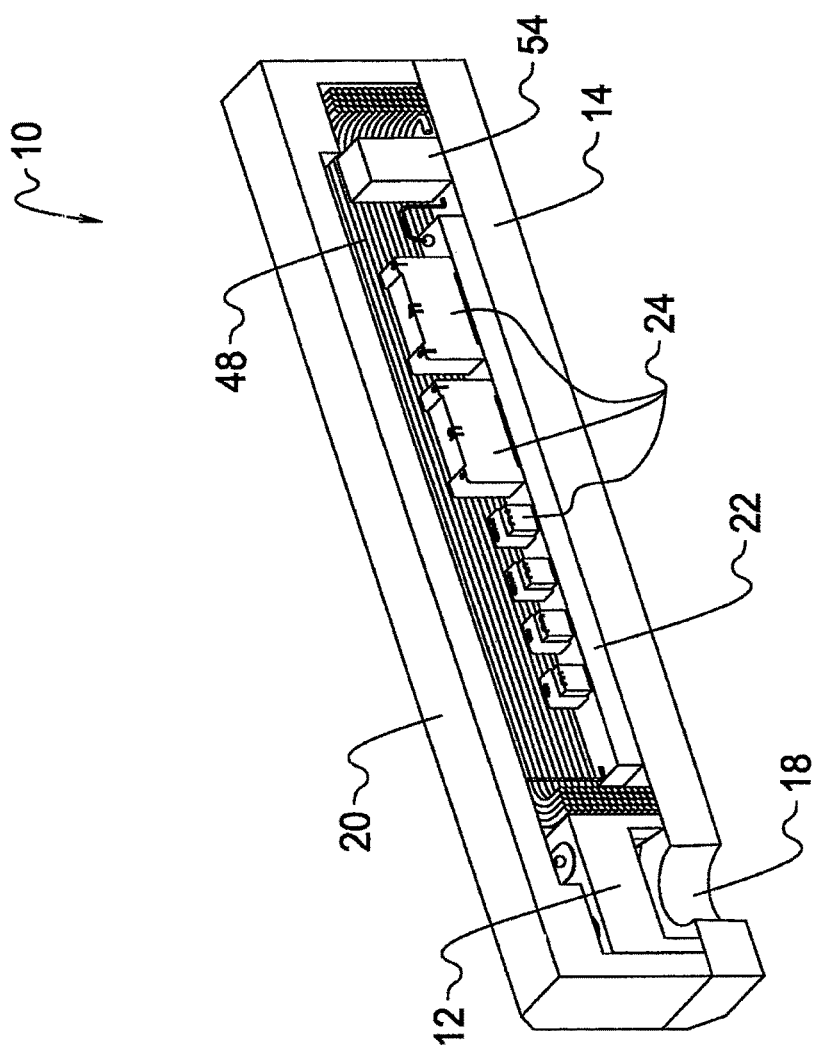
FIG. 11 is a cross sectional perspective view taken along lines A-A of FIG. 4 including the battery or high energy storage device.

Referring to FIG. 11 there is shown a cross-sectional view of the pressure sensor module 10 including the integrated circuit 22 upon which is mounted, circuit components 24, a battery 54 or a high energy storage device that is positioned next to the circuit component 24 with such components being encircled by internal coil 48. The compact component packaging shown in FIG. 11 provides for efficient pressure sensor operation while minimizing the overall size of the pressure sensor module 10.

An Example Application of the Pressure Sensor Module in an Implantable Shunt System for Improved Treatment of Hydrocephalus As previously described, hydrocephalus is a medical condition whereby for any number of reasons, the volume of CSF increases within a patient's head and brain and the size of cranial ventricles increases with an attendant increase of pressure and injury in the head/brain area. Implantable shunt systems have been used in the past to treat hydrocephalus by providing a fluid conduit for excess CSF to drain to another part of the body such as the abdominal cavity or to a chamber of the heart. In the case of draining the CSF to the abdomen, the shunt is called a ventriculoperitoneal shunt and in the case of draining the CSF to the heart, the shunt is called a ventriculoatrial shunt. As is known in the art, shunt is understood to mean: to move a body fluid such as cerebrospinal fluid from one place to another. In terms of a device, a shunt is understood to be synonymous with a catheter (tube) and thus a shunt and a catheter can be used interchangeably, for carrying cerebrospinal fluid, for example, from a ventricle in the brain to another area of the body. A lumen in biology is understood to be the inside space of a tubular structure such as a shunt or catheter. Typically, the implantable shunt includes a pressure valve to regulate the flow rate of the CSF at a regulated pressure setting. The valve may be a fixed pressure valve where the flow rate is regulated at a predetermined pressure setting or an adjustable pressure valve where the flow rate is regulated on a pressure setting that can be adjusted based upon physiological parameters. Pressure valves are known in the art, for example Strata Valves offered by Medtronic, Inc. and Sophy® and Polaris® valves offered by Sophysa and thus not discussed here in detail.

Figure 12:
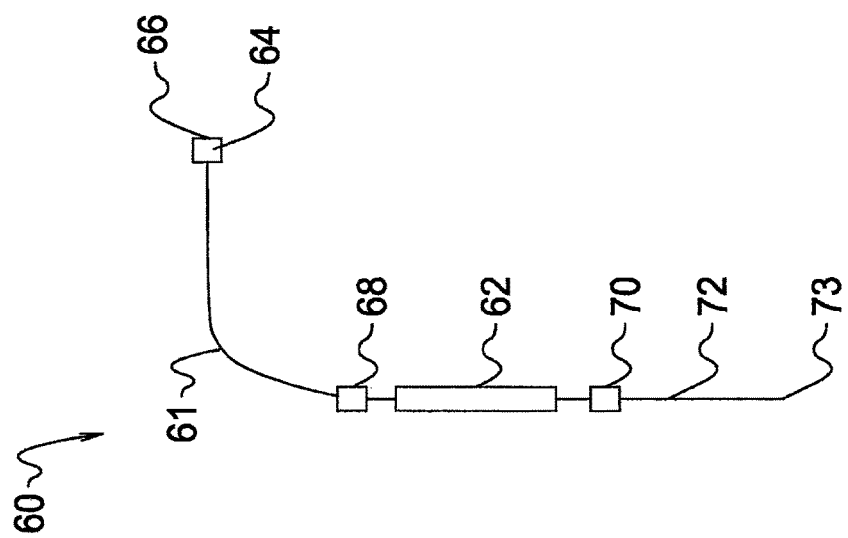
FIG. 12 is a schematic drawing of pressure sensors and flow control valve disposed along an implantable shunt.

A common cause of shunt failure is blockage of the CSF flow path in the shunt which can occur at different locations of the shunt. For example, blockage may occur at the tip of the shunt (called the ventricular catheter 61) where the CSF enters the shunt or at the pressure valve or at the outlet or distal catheter portion of the shunt 60 (also called the drainage catheter) as a result of tissue growth over, around or into the catheter. To address the desirability of complete pressure monitoring in an implantable shunt system, an example embodiment of the present invention shown in FIG. 12, includes measuring the pressure in the cerebral ventricles of the brain and inside the shunt 60, that is, within the lumen 78 of the shunt 60. More specifically and with reference to FIG. 12, shunt 60 includes a fluid flow control valve 62, a first pressure sensor 64 positioned at the tip 66 of the ventricular catheter 61, a second pressure sensor 68 (upstream pressure sensor) positioned in the shunt 60 between the first pressure sensor 64 and the fluid flow control valve 62, preferably positioned proximate to or immediately before and upstream from the fluid flow control valve 62, and a third pressure sensor 70 (downstream pressure sensor) positioned in the shunt 60 between the fluid flow control valve 62 and the drainage catheter portion 72 of shunt 60, preferably proximate to the fluid flow control valve 62. It is to be understood that the pressure sensors 64, 68 and 70 are formed in accordance with the construct of the pressure sensor module 10 discussed above. From a positioning standpoint, the tip 66 is intended to be positioned at the site in the patient's head where pressure is to be monitored and where CSF is to be withdrawn and the inlet holes 65 are the point of entry or inlet of CSF into shunt 60. The drainage catheter portion 72 has an outlet 73 that may be extended to terminate in the abdomen or in the heart as the case may be and through which the CSF is discharged.

Figure 16:
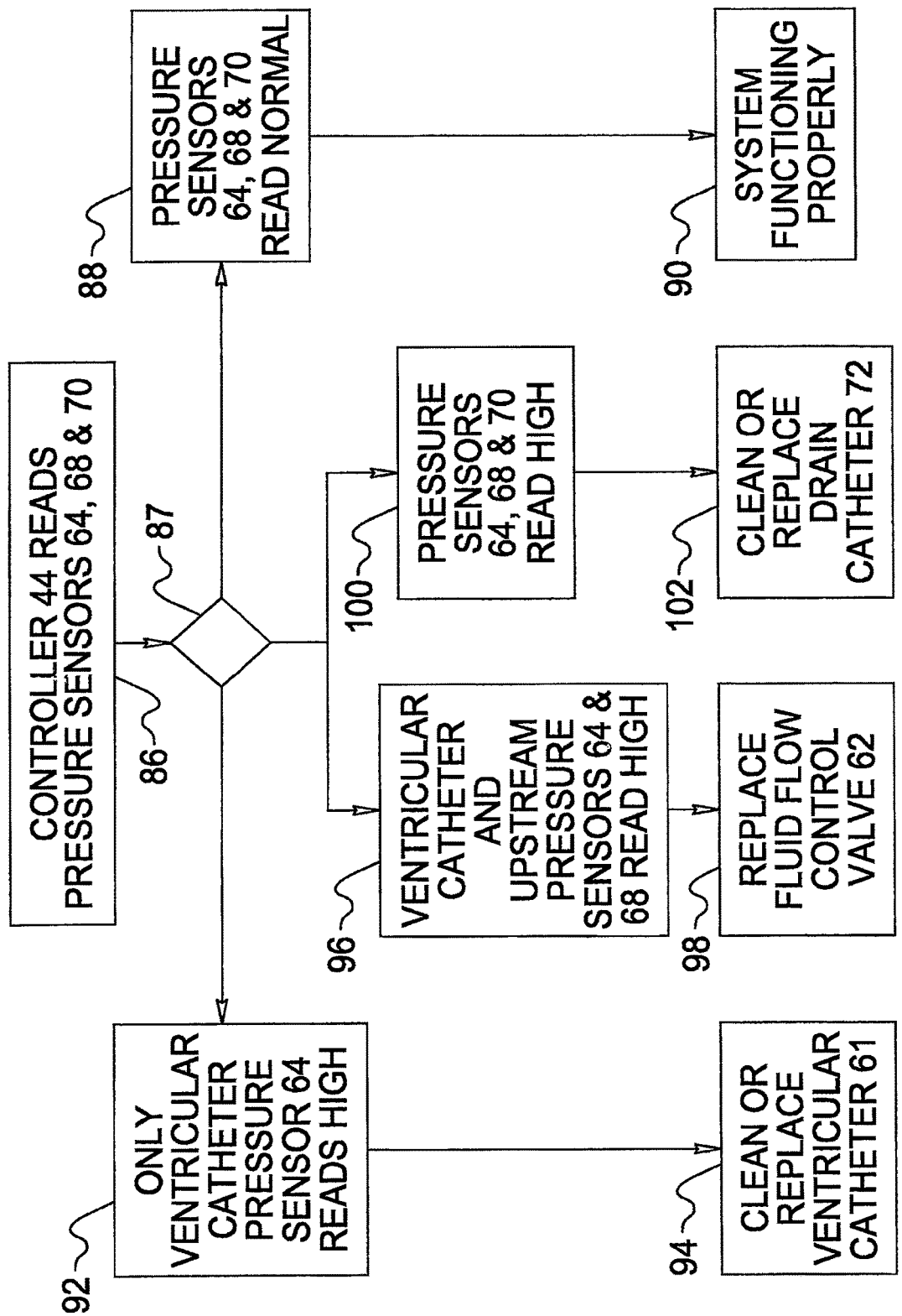
FIG. 16 is a flow chart of patient treatment options based on pressure sensor readings.

In terms of patient care, a shunt system incorporating the uniquely positioned three pressure sensors as described above provides unambiguous information about the functioning of the shunt system. The information may be utilized by a caregiver or in the case of an automated monitoring system the information may be used to trigger alarms for the attention of health care professionals. The flow chart of FIG. 16 presents patient treatment options based upon the various pressure sensor readings described below. The flow chart of FIG. 16 can also be understood as a method for controller 44 to determine the operational status of shunt 60 and generate status messages to the patient and/or to a doctor. The status messages can be of various types, such as an audible alert, LED status lights or a visual message shown on display 46, or a message sent wirelessly by a cell phone network to a doctor or a hospital.

With regard to patient treatment options, if a patient presents with symptoms of elevated ICP, information from the sensors read by controller 44 (block 86) will help identify the sources of potential danger depending upon the detected pressure readings read by the external controller 44 which then determines which option to pursue (block 87) according to the following scenarios to thereby provide an indication or instruction for taking corrective action:

(A) All three pressure sensors provide normal range pressure readings (block 88) and readings from the sensor located in the ventricle are fluctuating in rhythm with blood pressure (BP) systole. Under such conditions, the diagnosis can be made that the patient's symptoms are unrelated to a malfunctioning shunt (block 90);

(B) The pressure sensor 64 (also known as ventricular pressure sensor) pressure reading is elevated relative to the other two pressure sensors (block 92). Under such conditions, the diagnosis can be made that the ventricular catheter is plugged and therefore not allowing excess CSF to enter the shunt and drain through the shunt to the drainage site. In such case, the ventricular catheter 61 will require cleaning or replacement (block 94) as a result potentially of any passageways in the shunt being occluded by choroid plexus;

(C) Both the ventricular pressure sensor 64 and pressure sensor 68 provide elevated pressure readings relative to pressure sensor 70 (block 96). Under such conditions, the diagnosis can be made that the valve 62 is malfunctioning and requires either cleaning or replacement (block 98); and (D) All three pressure sensors provide elevated pressure readings (block 100). Under such conditions, the drainage catheter portion 72 is plugged and requires clearing or replacement (block 102).

Figure 13:
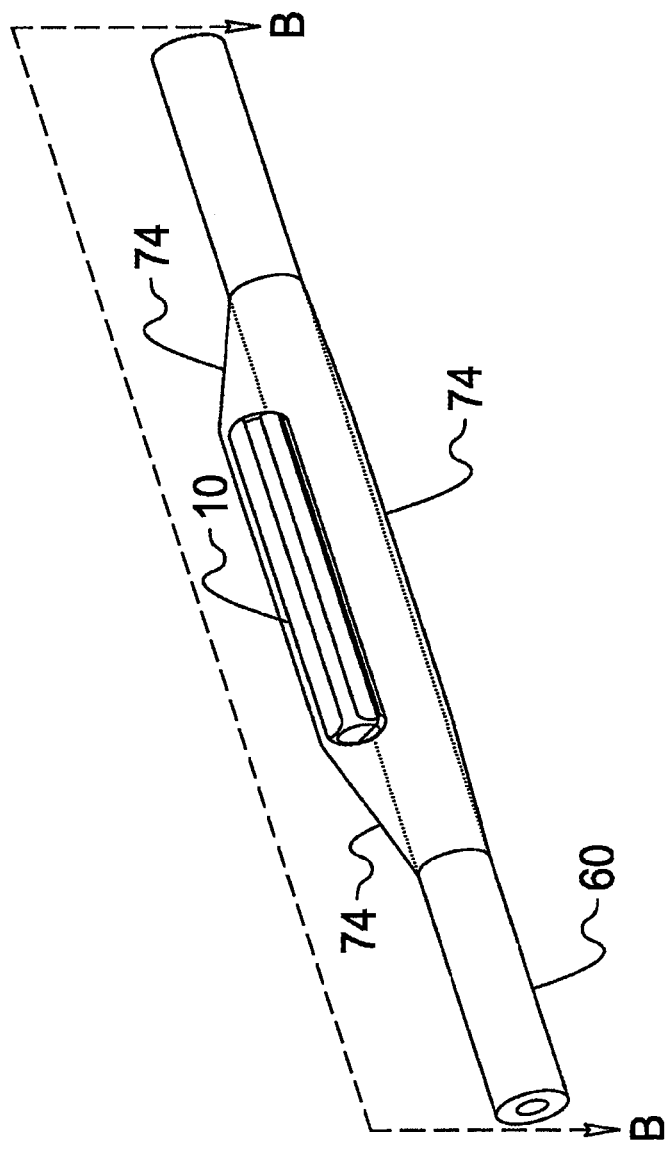
FIG. 13 is a phantom perspective view of a pressure sensor mounted on an implantable shunt.

Referring now to FIG. 13, there is shown in phantom perspective view, a portion of the shunt 60 to which is secured a pressure sensor module 10. The shunt 60 may be formed from any one of a number of biocompatible elastomeric materials satisfying the Food and Drug Administration's (FDA) requirements for implantable devices as is known in the art. The pressure sensor module 10 is secured to the shunt 60 by means of constraining over-molding 74, preferably utilizing the same material used for shunt 60. Accordingly, the pressure sensor module 10 remains stationary in place relative to shunt 60 independent of any shunt movements. As will be discussed below, this is an important feature of the Implantable Shunt System in order to maintain the aperture 18 of the pressure sensor module in strict and continual alignment with a corresponding orifice 76 in shunt 60.

Figure 14:
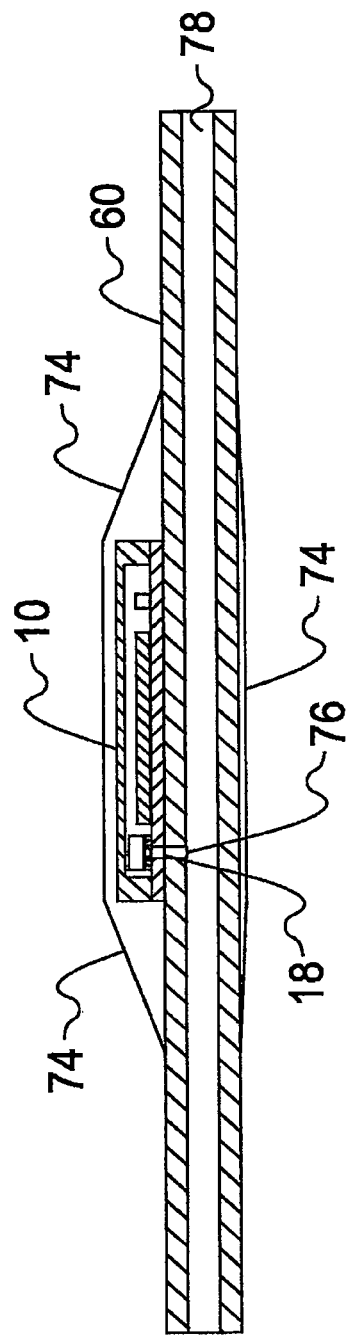
FIG. 14 is a partial cross-sectional view of a pressure sensor mounted on an implantable shunt.
Figure 15A:
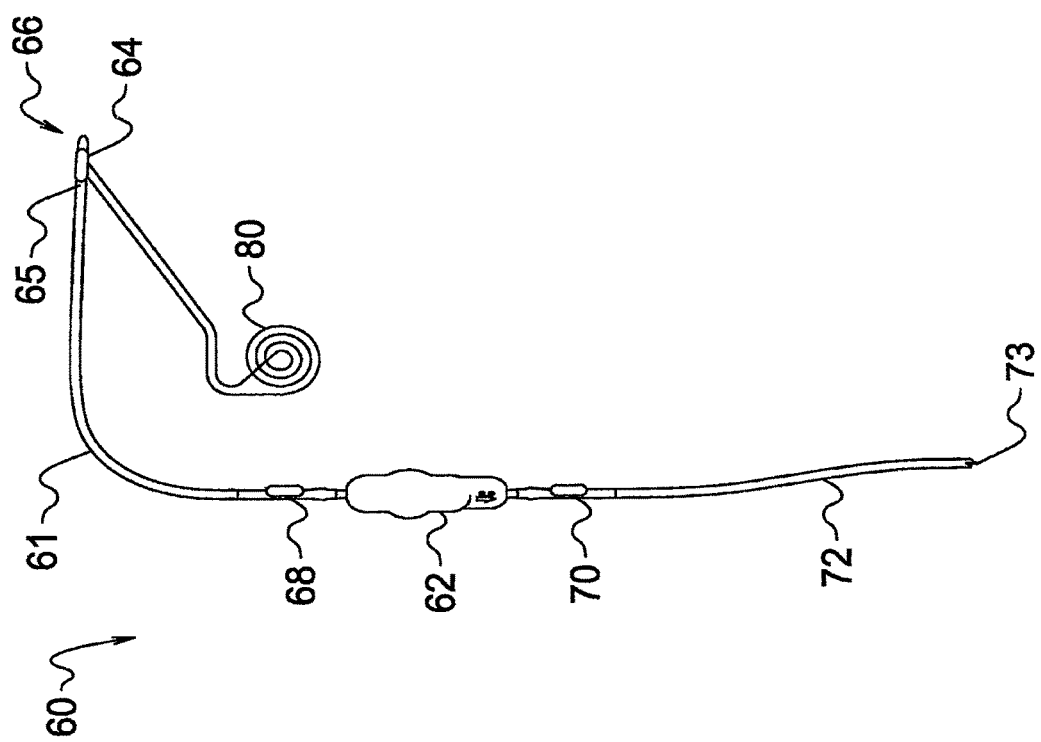
FIG. 15A is a schematic view of three pressure sensors mounted on an implantable shunt wherein only one pressure sensor is attached to a coil for power and data transmission.

More specifically and with reference to the configuration shown in the cross-sectional view of FIG. 14, which relates to pressure sensors 68 and 70, in order to monitor the pressure of CSF in lumen 78, an orifice 76 is provided in shunt 60 and the pressure sensor module 10 is positioned so that aperture 18 is in constant alignment with orifice 76 so that fluid communication is established between the shunt 60 and pressure sensor module 10. Accordingly, CSF pressure will be directly, continually and reliably monitored at the desired site for transmission to external monitoring apparatus. An arrangement of a three pressure sensor configuration is shown in FIG. 15A wherein subcutaneous coil 80 is associated with pressure sensor 64 in a manner totally consistent with the configuration shown in and described for the arrangement shown in FIG. 6. As is noted, pressure sensors 68 and 70 are not associated with respective subcutaneous coils because such configuration contemplates that pressure sensors 68 and 70 are positioned sufficiently close to the patient's scalp so that a direct communication link between external coil 42 and such sensors is satisfactorily established without the need and use of subcutaneous coils.

Figure 15B:
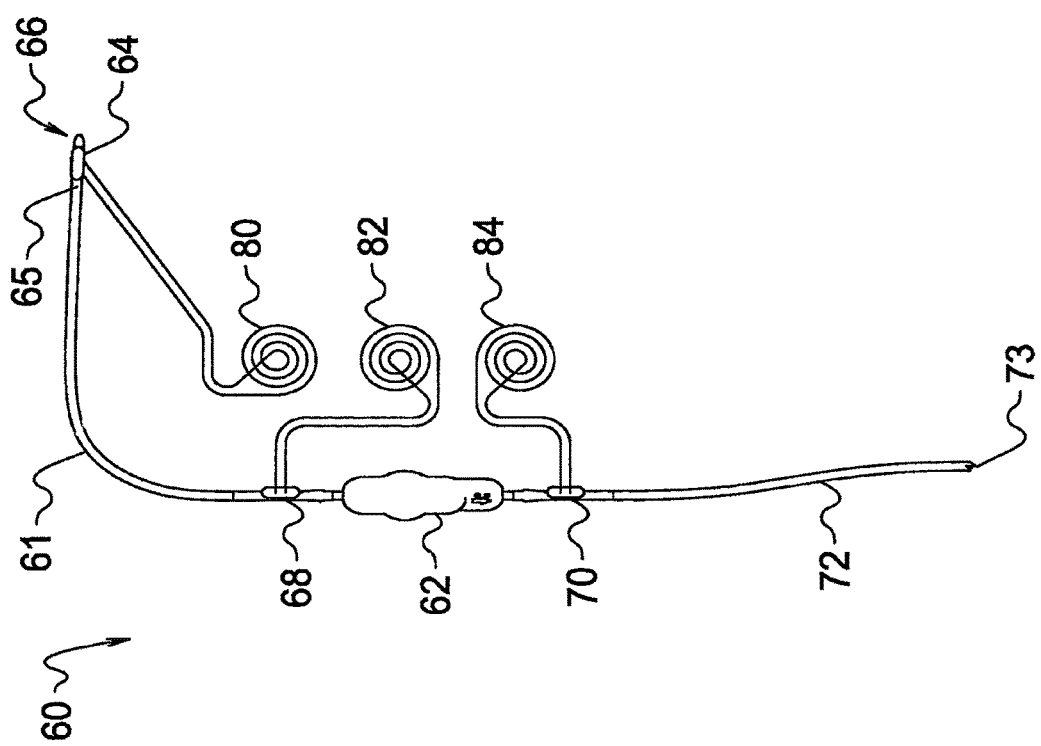
FIG. 15B is a schematic view of three pressure sensors mounted on an implantable shunt wherein each pressure sensor is attached to a respective coil for power and data transmission.

An arrangement wherein pressure sensors 64, 68 and 70 include subcutaneous coils 80, 82 and 84 respectively is shown in FIG. 15B. Each one of the subcutaneous coils 80, 82 and 84 is associated with a corresponding external coil (not shown) and controller 44 in a manner totally consistent with the configuration shown in and described for the embodiment of FIG. 6 and which is applicable for each one of the three pressure sensors 64, 68 and 70. The embodiment of FIG. 15B contemplates that, because of the positioning of pressure sensors 68 and 70, the communication link between the respective pressure sensors and the external coil 42 is better established using corresponding subcutaneous coils 82 and 84. In terms of a design choice, the external coils associated with pressure sensors 64, 68 and 70 respectively, may be coupled to an individual respective controller or a signal controller which is well within the capability of one skilled in the art. Similarly, a single external coil 42 may be used for communication with all three subcutaneous coils 80, 82 and 84 or in the alternative, three external coils may be used, each one of the coils used with a respective subcutaneous coil which is well within the capability of one skilled in the art.

Figure 15C:
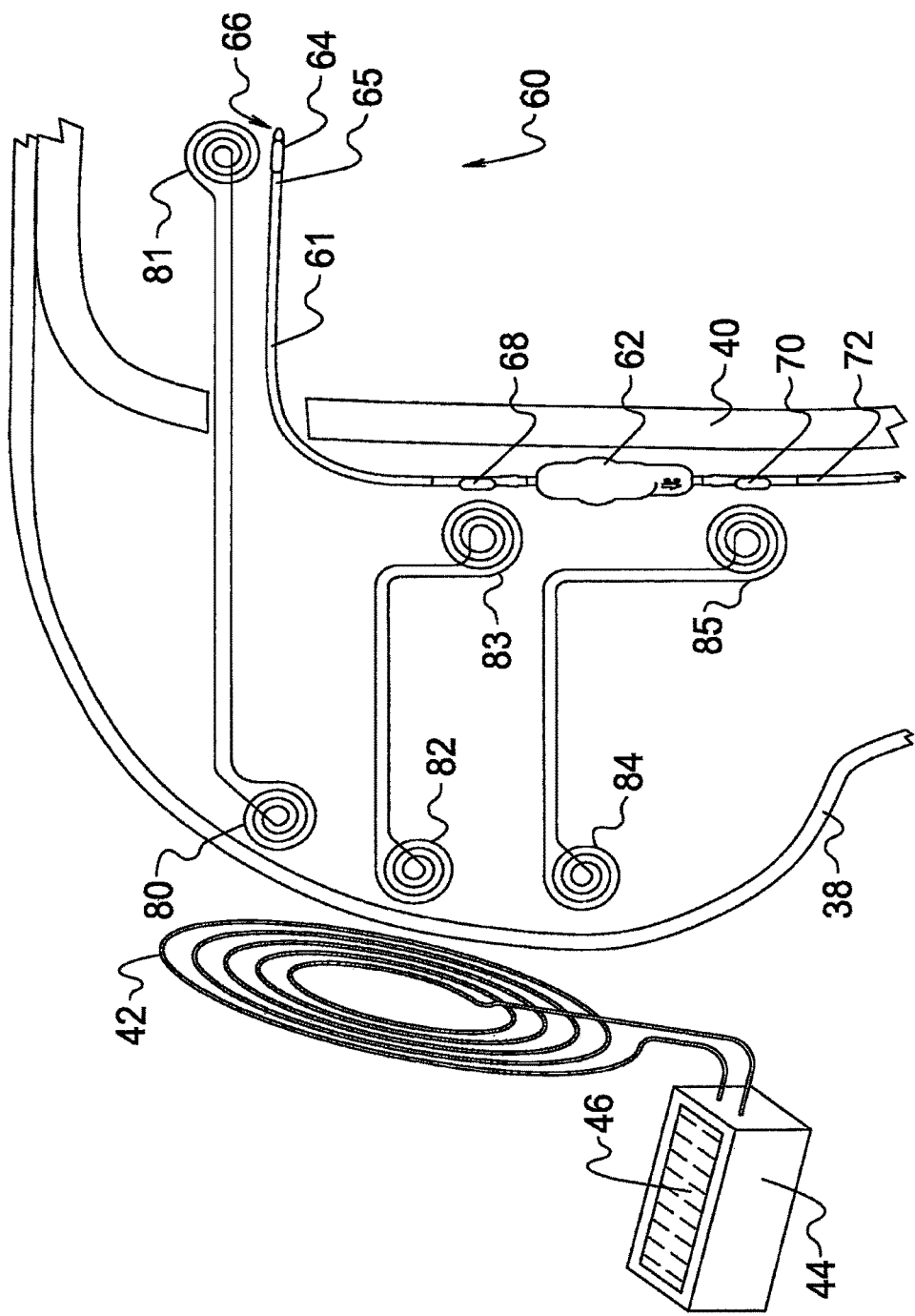
FIG. 15C is a schematic view of a complete system wherein three pressure sensors are mounted on an implantable shunt wherein each pressure sensor is attached to a respective coil for power and data transmission in association with an external controller.

Referring to FIG. 15C, there is shown an expanded view of an embodiment wherein pressure sensors 64, 68 and 70 utilize corresponding outside coils 81, 83 and 85 respectively which are coupled to subcutaneous coils 80, 82 and 84 respectively. In such cases, operation of the embodiment of FIG. 15C is totally consistent with the configuration shown in and described for the embodiment of FIG. 6 and which is applicable for each one of the three pressure sensors 64, 68 and 70. Optionally, a remote controller (not shown) can be wirelessly coupled to external controller 44 and provide control and monitoring capability to the Implantable Shunt System from a location remote from controller 44.

Figure 17:
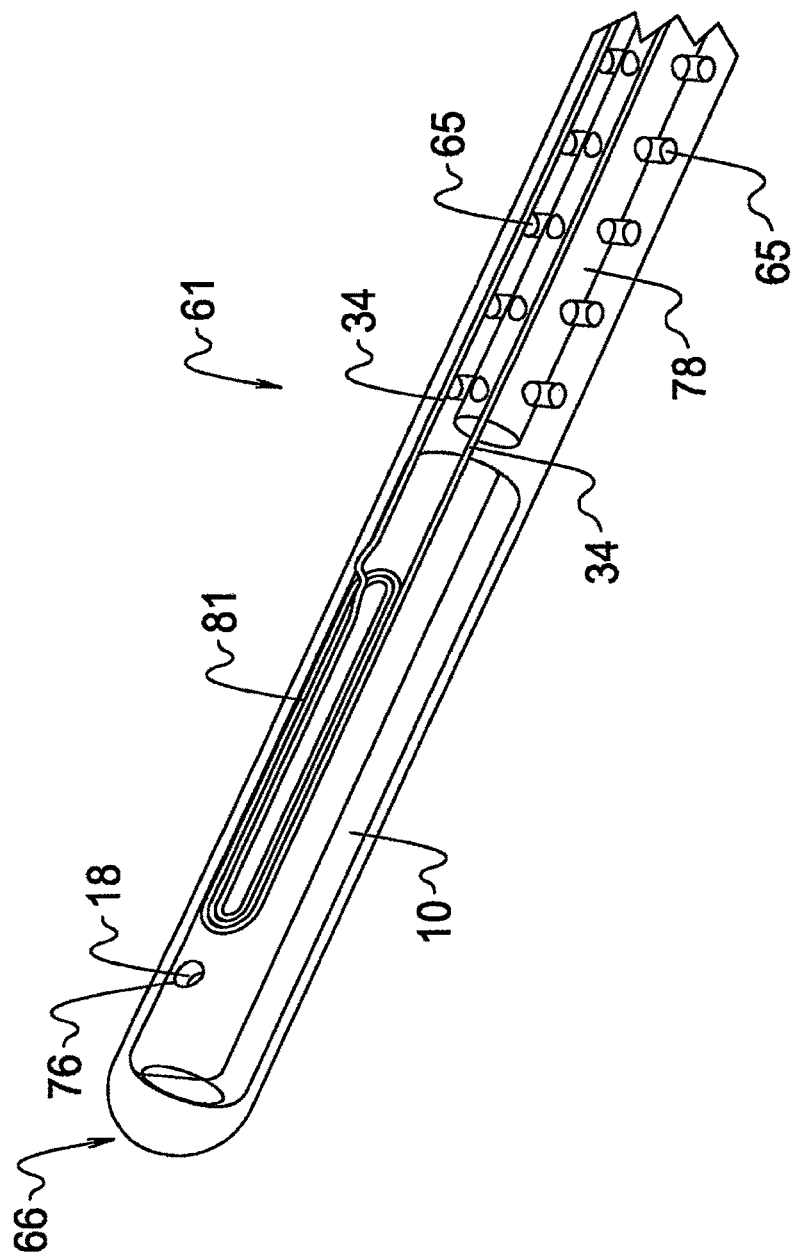
FIG. 17 is a perspective view of a pressure sensor module and associated electromagnetic coils embedded within the tip portion of a shunt.

Referring now to FIG. 17 there is shown in phantom perspective view, a pressure sensor module 10 that undertakes the function of pressure sensor 64 as shown at least in FIGS. 12 and 15A-15C. Positioned coaxially within shunt 60 at the tip 66 of ventricular catheter 61, the pressure sensor module 10 detects the fluid pressure at the tip 66 through aperture 18 which is in alignment with an orifice 76 in shunt 60. The tip 66 is sealed and the pressure sensor module 10 is small enough and is embedded within shunt 60 so that during insertion the shunt 60 will not displace more brain tissue than it would for a shunt not containing the pressure sensor module 10. As shown in FIG. 17, the lumen 78 does not extend to the pressure sensor module 10 and entry of CSF into shunt 60 is through inlet holes 65. Accordingly, with the exception of the aperture 18, the pressure sensor module 10 is completely isolated from CSF and the contents of shunt 60. Moreover, the configuration of FIG. 17 provides for the measurement of fluid pressure in the brain outside of ventricular catheter 61 without blocking fluid flow in lumen 78. In the event that the inlet holes 65 become blocked by tissue or debris, the CSF will no longer flow into lumen 78 and pressure sensor module 10 will measure a higher pressure than upstream pressure sensor 68.

Furthermore, the outside coil 81, which functions in a manner consistent with the placement and operation of outside coil 32 shown in FIG. 6, is placed against pressure sensor module 10 and is embedded in the ventricular catheter 61 portion of shunt 60. The leads 34 may be attached to the inner surface of the lumen 78 or to the outer surface of ventricular catheter 61 or embedded within the shunt in order to provide a smooth, non-protruding profile. Outside coil 81 is electrically coupled to subcutaneous coil 80 and coil 80 is electromagnetically coupled to external coil 42 as shown in FIG. 15C. As has been previously discussed, controller 44 is configured to send power to pressure sensor module 10 and to receive data, such as pressure sensor readings from pressure sensor module 10.

Although the preceding description describes various embodiments of the system, the invention is not limited to such embodiments, but rather covers all modifications, alternatives, and equivalents that fall within the spirit and scope of the invention. Since many embodiments of the invention can be made without departing from the spirit and scope of the invention, the invention resides in the claims hereinafter appended.

What is claimed is:

1. A dual stage power transfer system comprising:
an implantable medical device, the implantable medical device comprising an internal coil encircling an integrated circuit, a circuit component, and/or a battery;
a first coil positioned external of the implantable medical device and in proximity to the internal coil for electromagnetic coupling therewith, the first coil being attached to the implantable medical device; and
a subcutaneous coil configured for subcutaneous placement, the subcutaneous coil being configured to electromagnetically couple with an external coil placed externally of a patient, the subcutaneous coil being smaller in size than the external coil,
wherein the subcutaneous coil is configured to receive a power signal from the external coil through the electromagnetic coupling between the subcutaneous coil and the external coil and transfer the power signal to the first coil, and
wherein the first coil is positioned in alignment with the internal coil and configured to transfer the power signal to the internal coil through the electromagnetic coupling between the first coil and the internal coil.

2. The system of claim 1, wherein the internal coil is configured to transfer a data signal to the first coil through the electromagnetic coupling between the first coil and the internal coil, the first coil is configured to transfer the data signal to the subcutaneous coil, and the subcutaneous coil is configured to transfer the data signal to the external coil through the electromagnetic coupling between the subcutaneous coil and the external coil.

3. The system of claim 1, wherein the implantable medical device comprises a hermetically sealed housing, the internal coil being inside the hermetically sealed housing, and wherein the first coil is outside the hermetically sealed housing.

4. The system of claim 3, wherein the first coil is attached to an external surface of the hermetically sealed housing.

5. The system of claim 1, wherein the first coil is attached to an external surface of the implantable medical device.

6. The system of claim 1, further comprising a first conductive lead and a second conductive lead, wherein the first coil has a first terminal and a second terminal at opposite ends of the first coil, the subcutaneous coil has a first terminal and a second terminal at opposite ends of the subcutaneous coil, the first conductive lead connects the first terminal of the first coil with the first terminal of the subcutaneous coil, and the second conductive lead connects the second terminal of the first coil with the second terminal of the subcutaneous coil.

7. The system of claim 6, wherein the first conductive lead or the second conductive lead may be coiled.

8. The system of claim 6, wherein the first conductive lead and the second conductive lead extend through a bone.

9. The system of claim 1, wherein the power signal is transferred from the subcutaneous coil to the first coil.

10. The system of claim 1, wherein the subcutaneous coil is configured to be positioned remote from the first coil.

11. The system of claim 1, wherein a device parameter of the implantable medical device is configured to be adjusted by an external controller coupled to the external coil.

12. The system of claim 1, wherein a single continuous coiled wire structure comprises the first coil and the subcutaneous coil, and wherein the first coil and the subcutaneous coil form the opposite ends of the continuous coiled wire structure.

13. The system of claim 1, wherein the first coil is positioned in one-to-one alignment with the internal coil.

14. A method of dual stage power transfer for use with an implantable medical device, comprising:
receiving, by a subcutaneous coil, a power signal from an external coil through electromagnetic coupling between the subcutaneous coil and the external coil, the subcutaneous coil being smaller in size than the external coil, the subcutaneous coil being configured for subcutaneous placement;
transferring, by the subcutaneous coil, the power signal to a first coil, the first coil being positioned external of the implantable medical device and in proximity to an internal coil for electromagnetic coupling therewith, the implantable medical device comprising the internal coil encircling an integrated circuit, a circuit component, and/or a battery, the first coil being positioned in alignment with the internal coil and attached to the implantable medical device; and
transferring, by the first coil, the power signal to an internal coil through electromagnetic coupling between the first coil and the internal coil.

15. The method of claim 14, further comprising:
transferring, by the internal coil, a data signal to the first coil through the electromagnetic coupling between the first coil and the internal coil;
transferring, by the first coil, the data signal to the subcutaneous coil; and
transferring, by the subcutaneous coil, the data signal to the external coil through the electromagnetic coupling between the subcutaneous coil and the external coil.

16. The method of claim 14, wherein the implantable medical device comprises a hermetically sealed housing, the internal coil being inside the hermetically sealed housing, and wherein the first coil is outside the hermetically sealed housing.

17. The method of claim 16, wherein the first coil is attached to an external surface of the hermetically sealed housing.

18. The method of claim 14, wherein the first coil has a first terminal and a second terminal at opposite ends of the first coil, the subcutaneous coil has a first terminal and a second terminal at opposite ends of the subcutaneous coil, a first conductive lead connects the first terminal of the first coil with the first terminal of the subcutaneous coil, and a second conductive lead connects the second terminal of the first coil with the second terminal of the subcutaneous coil.

19. The method of claim 14, wherein the power signal is transferred from the subcutaneous coil to the first coil.

20. The method of claim 14, wherein the subcutaneous coil is configured to be positioned remote from the first coil.

21. The method of claim 14, further comprising adjusting, by an external controller coupled to the external coil, a device parameter of the implantable medical device.

22. A dual stage power transfer system comprising:
- an implantable medical device, the implantable medical device comprising an internal coil encircling an integrated circuit, a circuit component, and/or a battery;
- a first coil positioned external of the implantable medical device and in proximity to the internal coil for electromagnetic coupling therewith, the first coil being attached to the implantable medical device;
- an external coil coupled to an external controller
- a subcutaneous coil configured for subcutaneous placement, the subcutaneous coil being configured to electromagnetically couple with the external coil placed externally of a patient; and
- wherein the subcutaneous coil is configured to receive a power signal from the external coil through the electromagnetic coupling between the subcutaneous coil and the external coil and transfer the power signal to the first coil,
- wherein the subcutaneous coil is smaller in size than the external coil, and
- wherein the first coil is positioned in alignment with the internal coil and configured to transfer the power signal to the internal coil through the electromagnetic coupling between the first coil and the internal coil.

\* \* \* \* \*